United States Patent [19]

Montaldi

[11] Patent Number: 4,966,130

[45] Date of Patent: Oct. 30, 1990

[54] ONE-PIECE DISPOSABLE SPECULUM

[76] Inventor: David H. Montaldi, 2358 Howell Mill Rd., NW., Atlanta, Ga. 30318

[21] Appl. No.: 470,574

[22] Filed: Jan. 26, 1990

[51] Int. Cl.$^5$ .............................................. A61B 1/30
[52] U.S. Cl. .................................................. 128/17
[58] Field of Search ................................ 128/3, 17, 18

[56] References Cited

U.S. PATENT DOCUMENTS

| | | | |
|---|---|---|---|
| D. 232,779 | 9/1974 | Olson | D24/2 |
| 325,647 | 9/1885 | Baily | 128/17 |
| 832,201 | 10/1906 | Kistler | 604/108 |
| 3,246,646 | 4/1966 | Murphy, Jr. | 128/17 |
| 3,528,409 | 9/1970 | Bruder | 128/17 |
| 3,716,047 | 2/1973 | Moore et al. | 128/18 |
| 3,736,919 | 6/1973 | Cotey | 128/17 |
| 3,745,992 | 7/1973 | Poirier | 128/17 |
| 3,769,980 | 11/1973 | Karman | 128/17 X |
| 3,835,843 | 9/1974 | Karman | 128/17 |
| 3,841,318 | 10/1974 | Olson | 128/20 |
| 3,890,961 | 6/1975 | Moore et al. | 128/17 |
| 4,432,351 | 2/1984 | Hoary | 128/17 |
| 4,766,887 | 8/1988 | Cecil, Jr. et al. | 128/17 |
| 4,854,300 | 8/1989 | Corbo | 128/17 X |

Primary Examiner—William H. Grieb
Attorney, Agent, or Firm—Cushman, Darby & Cushman

[57] ABSTRACT

A disposable speculum made of a unitary molded plastic construction. Upon folding, a pair of elongated members form opposing jaws or blades which are pivotally attached to a central ring. A handle portion is formed on an end of the lower blade and can be used to insert the speculum into a body cavity. Once inside a body opening, the opening can be dilated by pushing forward on the upper blade to elevate the upper blade from the lower blade of the speculum. The blades can be adjustably held at a desired opening size by support rods formed near the handle end of the speculum.

3 Claims, 2 Drawing Sheets

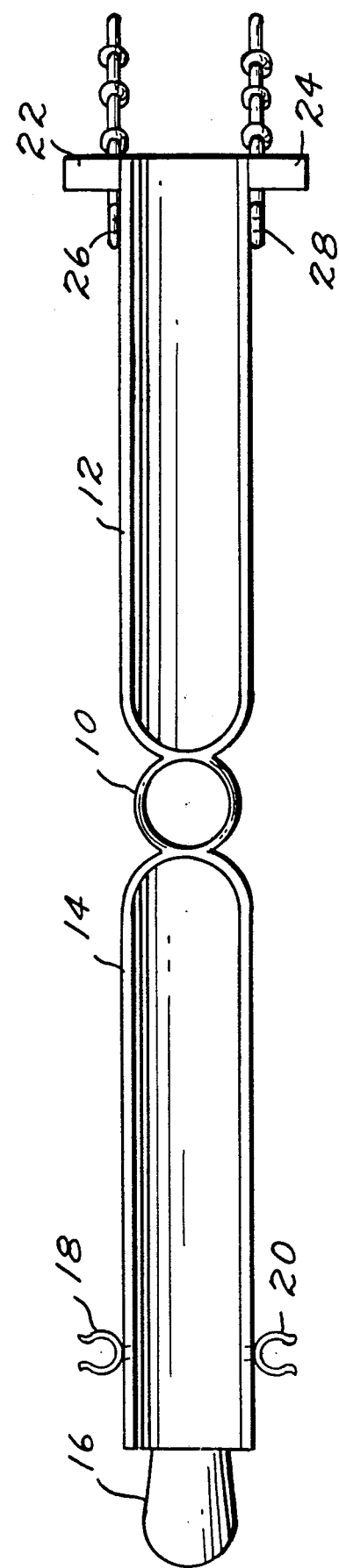

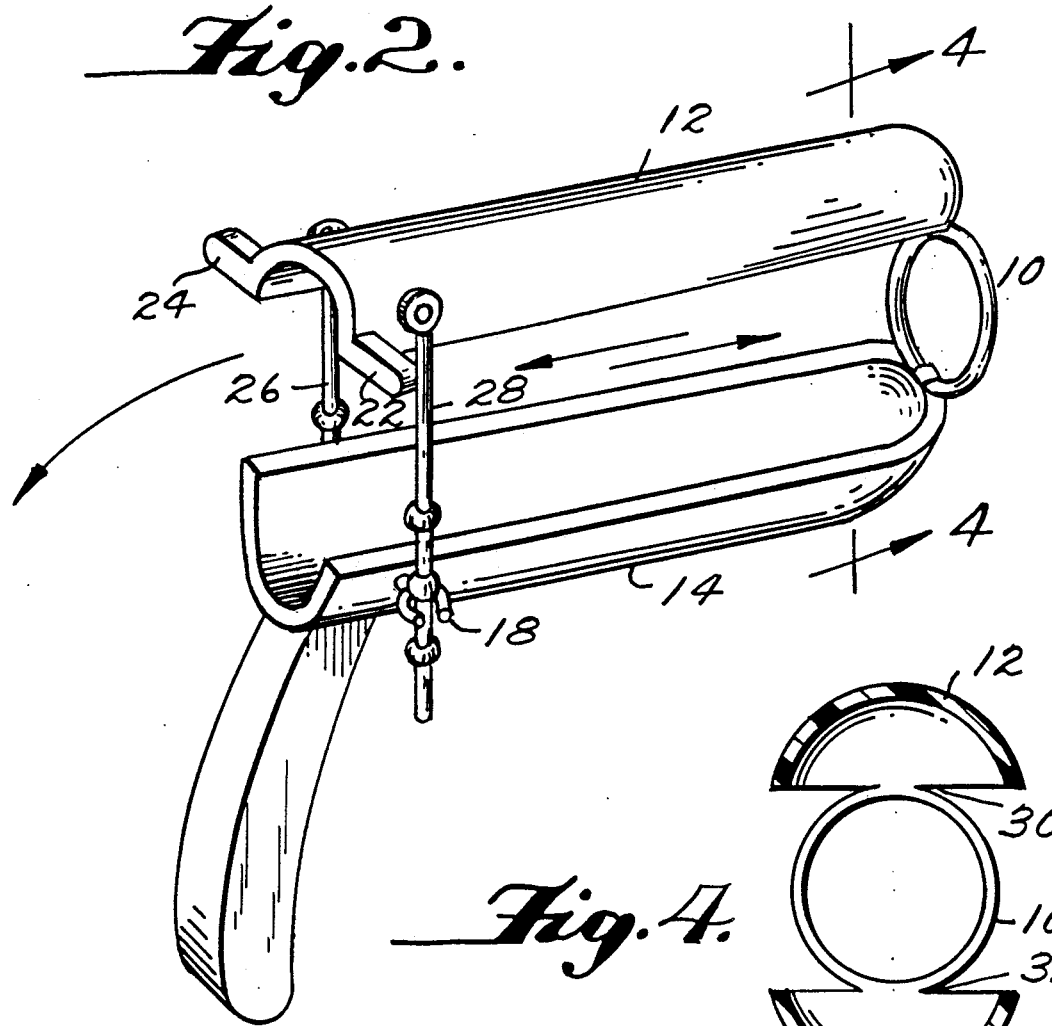
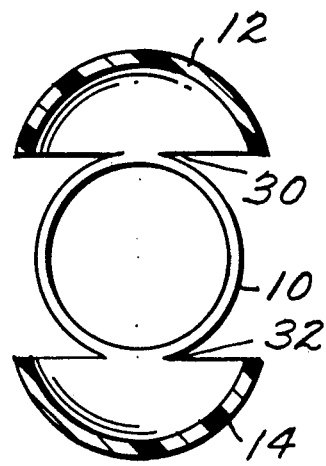
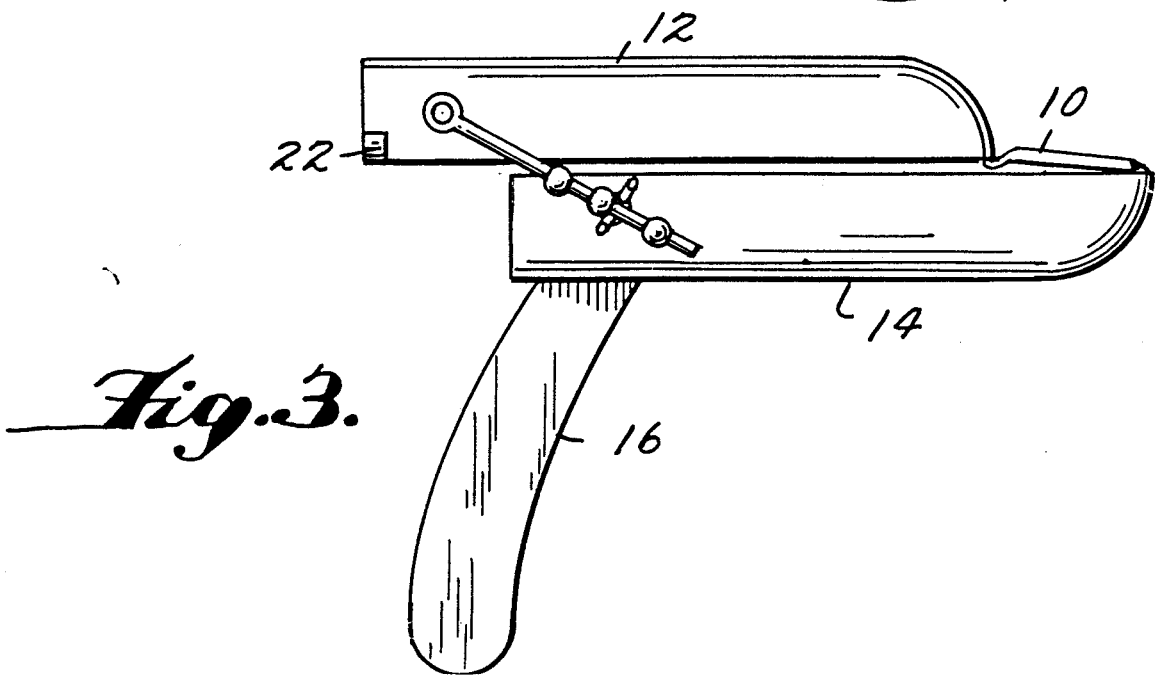

ONE-PIECE DISPOSABLE SPECULUM

BACKGROUND OF THE INVENTION

1. Field of the Invention

This invention relates generally to medical examination devices, and more particularly, to a one piece disposable speculum for use in examining body orifices.

2. Prior Art

Medical examination devices of the general class to which this invention belongs are well known in the art and are utilized to examine body orifices such as vagina, anus, ear canal, etc. A typical medical speculum for this purpose as shown in U.S. Pat. No. 3,246,646 has a pair of elongate body members disposed side by side and having confronting handles at one end and confronting jaws at the other end. Between the handles and jaws are pivot means which join the members in such a way that swinging of the handles towards one another spreads the jaws. The handles are connected by a pivot screw or the like and may be set to lock the speculum jaws in a spread position. In the spread position, an opening exists centrally through the speculum through which an examining physician may view the interior of a body orifice being examined.

While some of the existing medical specula as shown in U.S. Pat. No. 3,890,961, are of the disposable type, they possess certain deficiencies which this invention seeks to overcome. The existing instruments are often of the two or three piece construction which must be fitted together after manufacture or prior to use. Additionally, the disposable speculum developed heretofore have afforded less than a full range of adjustments permitted by more expensive metal instruments. Therefore, it is desirable to have a one piece inexpensive disposable speculum which has a wide range of adjustments for use in inspecting body orifices.

Specula of a two or three piece construction are known in the art. These specula contain a hinge at or near the handle portion of the speculum. A one piece integral formed speculum is shown in U.S. Pat. No. 3,841,318. It fails to have the adjustability of opening size as do the designs employing a two or three piece construction. There is a need for a one piece integrally formed speculum having full adjustability.

SUMMARY OF THE INVENTION

The present invention is a one piece disposable speculum comprising a unitary molded pair of elongated members pivotally attached to a central ring. When folded together the unitary members form opposing upper and lower blades along the length of the speculum with a handle at one end of the lower blade. Attached to one end of the upper blade is an adjustable support means which mates with the lower blade to maintain a desired opening size.

By pushing the upper blade forward, the upper blade moves from a linear position in a vertical direction to form a spaced-apart confronting jaw thereby opening the speculum inside the body cavity. The adjustable support rods attached to the upper jaw member can be fastened into holders on the handle portion of the lower jaw member to dilate the body opening to be inspected.

BRIEF DESCRIPTION OF THE DRAWINGS

FIG. 1 is a top plan view of the present invention;

FIG. 2 is a perspective drawing of the present invention;

FIG. 3 is a side view of the present invention as folded together; and

FIG. 4 is a sectional view taken along a Section 4—4 of FIG. 2 showing in cross-section the arrangement of the central ring pivotally attached to the elongated members.

DETAILED DESCRIPTION OF THE PREFERRED EMBODIMENT

Shown in FIG. 1 is a one piece unitary construction of the present speculum which may be molded in a one step operation to provide a central ring 10 pivotally connected to a pair of elongated members 12 and 14. Elongated member 14 has a handle portion 16 molded on an end portion of elongated member 14 distal from the central ring 10. Also formed on elongated member 14 are hooks 18 and 20. Elongated member 12 has rectangular shaped protrusions 22 and 24 and adjustable support rods 26 and 28.

When the one piece molded construction of FIG. 1 is folded together, it will form the speculum as shown in FIG. 2. The speculum of FIG. 2 is in its upright position. A central ring 10 pivotally connects the forward end of the upper blade 12 and lower blade 14. The lower blade 14 has a handle portion 16. Adjustable support rods 26 and 28 are shown engaged to the hooks 18 and 20.

The speculum can be injection molded or otherwise formed of a resilient plastic material. The plastic needs to be non-toxic and provide a warm to the touch feel. The linear layout of the speculum allows the design to be easily formed in a one-piece construction. The central ring is hingedly attached to the elongated members. This pivotal attachment can be a thinned region of plastic which allows the unitary construction to fold in predetermined places.

For insertion, the speculum may be flattened as shown in FIG. 3 to provide a more compact shape to ease insertion into a body orifice. The handle may be grasped by the hand of an examining physician and pushed forward into a body cavity. After entry is made into a body cavity for inspection, the thumb may be used on either hand to push against the back end of the upper blade on protrusions 22 and 24 to open up the speculum within the cavity to allow for visual inspection. Once the speculum in inserted in a body opening, the size of the opening can be adjusted by separating blade portions 12 and 14. Adjustable support rods 26 and 28 may be engaged into hooks 18 and 20 to maintain the desired dilation of the opening.

The hinge central ring 10 is hingedly attached to the upper blade 12 and the lower blade 14. This attachment may be made as a thinned out region as shown in FIG. 4. In the cross-sectional view of FIG. 4, thinned out regions 30, 32 join the central ring 10 to the blades 12 and 14.

The size of the central rings within a body cavity can be varied by the forward position of the upper blade with respect to the lower blade. The maximum opening is obtained when the upper and lower blades are inserted to the same depth. The rear opening of the speculum can be varied to obtain the desired dilation. The dilation can be maintained by adjustable support means.

While the invention has been described in connection with what is presently considered to the most practical and preferred embodiment, it is to be understood that the invention is not limited to the disclosed embodiments, but is intended to cover various modifications of an equivalent arrangements included within the spirit and scope of the appended claims.

What is claimed:

1. A one piece disposable speculum comprising:
   a pair of elongated members privotally joined together by a central ring;
   a handle formed at an one end of one of the elongated members distal from the central ring for urging the speculum into a body cavity; and
   adjustable support means attached to the distal end of the elongated members for holding the elongated members in an adjustable spaced-apart manner.

2. The speculum of claim 1 wherein the adjustable support means comprises rods attached to the distal end of one of the elongated member, the rods mating with hooks attached to the distal end of the other elongated member.

3. The speculum of claim 1 wherein the material of the speculum is plastic.

* * * * *